United States Patent [19]

White et al.

[11] 4,278,508

[45] Jul. 14, 1981

[54] METHOD OF DETECTING A CATHODIC CORROSION SITE ON A METALLIZED SUBSTRATE

[75] Inventors: Lawrence K. White, Cranbury; Robert B. Comizzoli, Belle Mead, both of N.J.; George L. Schnable, Lansdale, Pa.

[73] Assignee: RCA Corporation, New York, N.Y.

[21] Appl. No.: 93,214

[22] Filed: Nov. 13, 1979

[51] Int. Cl.³ ............................................ G01N 27/00
[52] U.S. Cl. .................... 204/1 T; 23/230 C; 250/372; 324/71 SN; 324/96; 324/158 R
[58] Field of Search .................... 204/1 C, 1 T; 252/301.19; 250/302, 372, 461 R; 73/86, 104; 324/438, 96, 71 SN, 158 D, 158 P; 23/230 C

[56] References Cited

U.S. PATENT DOCUMENTS

| | | | |
|---|---|---|---|
| 3,198,715 | 8/1965 | Fowler et al. | 204/1 C |
| 3,490,873 | 1/1970 | Corl | 23/230 |
| 3,530,045 | 9/1970 | Alburger | 204/1 T |
| 3,567,932 | 3/1971 | Alburger | 250/71 |
| 3,766,040 | 10/1973 | Wellborn, Jr. | 204/180 R |
| 4,035,641 | 7/1977 | Molina | 250/302 |
| 4,237,379 | 12/1980 | Deckert et al. | 250/302 |

OTHER PUBLICATIONS

J. Kruger, Use of Ellipsometry in the Study of Corrosion, *Corrosion*, vol. 22, No. 4 (4/66), p. 88.

*Primary Examiner*—Delbert E. Gantz
*Assistant Examiner*—William Leader
*Attorney, Agent, or Firm*—Birgit E. Morris; Donald S. Cohen; Thomas H. Magee

[57] ABSTRACT

A method of detecting a cathodic corrosion site on a metallized substrate comprises depositing molecules of a pH sensitive fluorescent dye adjacent a metallic surface of the substrate, the metallic surface having a corrosion site thereon characterized by a reduction of the hydronium ion to hydrogen ($2H^+ + 2e^- \rightarrow H_2$). An electrical bias is then applied across the metallic surface, and the fluorescent dye is exposed to ultraviolet (UV) radiation, whereby fluorescence is activated at the cathodic corrosion site.

11 Claims, 2 Drawing Figures

METHOD OF DETECTING A CATHODIC CORROSION SITE ON A METALLIZED SUBSTRATE

The Government has rights in this invention pursuant to Contract No. F30602-78-C-0276 awarded by the Department of the Air Force.

This invention relates to a method of detecting cathodic corrosion sites on a metallized substrate.

In electrical devices having metallic components, such as integrated circuit (IC) devices, the metallic components often corrode resulting in device failure. Corrosion sites are often difficult to detect before a significant amount of corrosion damage has occurred. A technique for identifying corrosion sites in their early stages before significant metallic deterioration occurs would be a powerful tool for metallized IC device reliability studies and in the study of corrosion processes themselves. The present invention discloses a technique for detecting cathodic corrosion sites on a metallic surface in the presence of an external DC bias. Such a technique is valuable for identifying the specific defects that produce corrosion sites, not only in metallized IC devices but in any metallized substrate where an external DC bias can be applied.

Fluorescent dyes have been utilized in various techniques for detecting defects in electrical devices. It is known to use fluorescent tracer compositions for the detection of surface defects in parts, as displayed elements (image-forming screens), or as marking materials. A fluorescent compound may be applied to a surface and then abraded from the surface to leave the compound in dents or scratches or the like. Certain fluorescent dyes are pH sensitive and exhibit fluorescence in the presence of actinic radiation, typically ultraviolet light, providing that the ambient pH is within a certain range of values.

The fluorescent dye fluorescein has been utilized for inspecting electrical devices such as integrated circuit devices which have gold-containing conductors covered by a protective layer of passivating material to determine the quality of the protective layer. Such a device is coated with fluorescein and exposed to ultraviolet (UV) radiation while applying electrical energy to two gold-containing conductors of the device. Fluorescence is observable in well passivated areas of the device but not in unpassivated or inadequately passivated areas.

The cathodic corrosion reaction which occurs on many metallized surfaces, such as aluminum, is a variation of the reduction of the hydronium ion to hydrogen, i.e., $2H^+ + 2e^- \rightarrow H_2$. This electrolysis reaction causes the localized pH to increase, resulting in appreciable current efficiency for corrosion of the metal. The site of this reaction generally occurs over a large area of the metallization in relation to a corresponding anodic reaction. We have discovered that a cathodic corrosion site on a metallic surface characterized by a reduction of the hydronium ion to hydrogen, can actually be visually detected by performing the present novel technique.

In accordance with the novel method of the present invention, we are able to detect a cathodic corrosion site on a metallized substrate by depositing molecules of a fluorescent dye adjacent a metallic surface of the substrate, the metallic surface having a corrosion site thereon characterized by a reduction of the hydronium ion to hydrogen $(2H^+ + 2e^- \rightarrow H_2)$. An electrical bias is then applied across the metallic surface, and the fluorescent dye is exposed to actinic radiation, whereby fluorescence is activated at the cathodic corrosion site.

Figure 1:
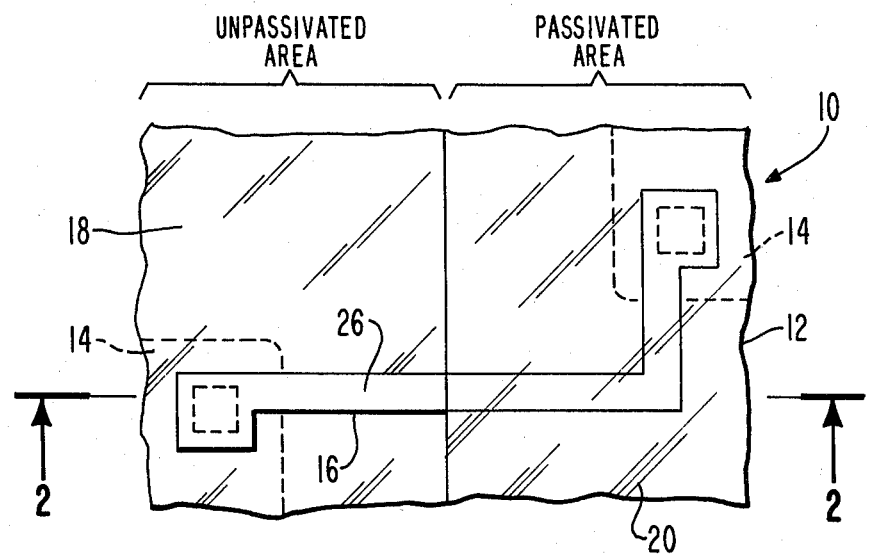
FIG. 1 is a plan view showing one embodiment of a metallized substrate.
Figure 2:
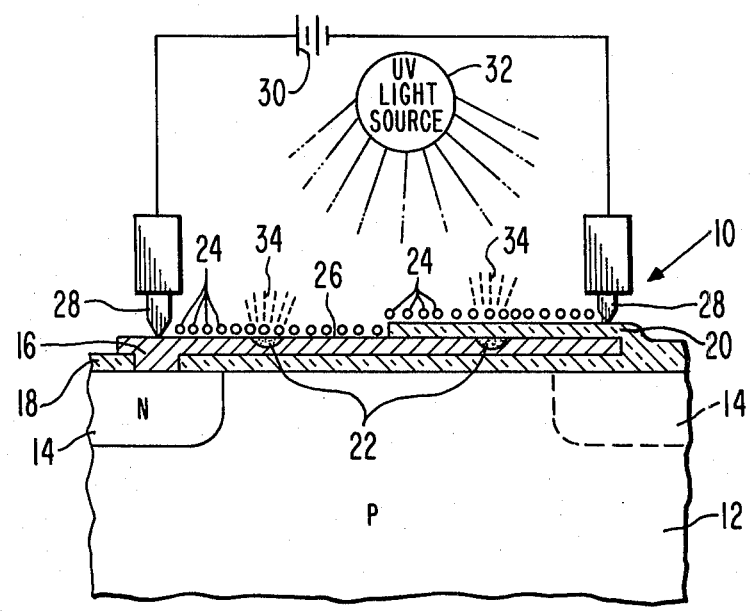
FIG. 2 is a cross-sectional view taken along line 2—2 of FIG. 1.

Referring to FIGS. 1 and 2 of the drawings, there is shown one embodiment of a metallized substrate comprising a monolithic integrated circuit (IC) device 10. For convenience, the present method will be described in detail with reference to detecting cathodic corrosion sites on the monolithic IC device 10. Such a device 10 is ordinarily fabricated by batch processes in which many devices are made simultaneously on a wafer 12 of one type semiconductor material in which regions 14 of the opposite type conductivity are formed. Different circuit elements within the device 10, including the regions 14, are connected typically by metallic conductors 16 deposited over a layer 18 of insulating material, such as thermally grown silicon dioxide. The metallic conductors 16 are typically protected by a layer 20 of a passivating material such as chemical-vapor-deposited (CVD) silicon dioxide. Defects in the layer 20 may arise during the fabrication process and cause cathodic corrosion sites 22 to occur in the conductors 16 at such defect locations. The cathodic corrosion reaction is characterized by a reduction of the hydronium ion to hydrogen and is capable of occurring at the surface of many metallic metals. In the present example, the metallic conductors 16 comprise aluminum.

The first step of the present method comprises depositing molecules 24 of a pH sensitive fluorescent dye adjacent the surface 26 of the aluminum conductor 16. It is not necessary that the dye molecules 24 be applied directly to the surface 26 of the conductor 16. As explained further below, the present detection method will also work if the molecules are deposited on the relatively thin insulating layer overlying the surface 26 of the conductor 16, such as the passivating layer 20 shown as the passivated area in FIG. 1.

The molecules 24 of the fluorescent dye have the capability of releasing a proton with relative ease $(HM \rightarrow H^+ + M^-)$. These molecules also have the property of exhibiting fluorescence in their deprotonated state in the presence of actinic radiation. Two fluorescent dyes which we found to be particularly effective in the present novel method are $\beta$-methylumbelliferone and $\beta$-naphthol.

The depositing step is performed preferably by coating the metallic conductor 16 and the passivating layer 20 with a fluorescent dye solution including molecules 24 of the dye dissolved in a solvent. In the present example, the fluorescent dye solution comprises $2 \times 10^{-4}$ moles of the dye dissolved in an excess of ethanol. Preferably, the dye solution is applied in a conventional wafer spinning apparatus in order to form a uniform film of the dye solution.

After depositing the solution of fluorescent dye molecules 24, the device 10 is placed in a humid ambient, preferably a nitrogen atmosphere of controlled relative humidity greater than about 30 percent. Humid ambients insure that the fluorescence will be activated and may well promote corrosive processes on IC devices. After applying the fluorescent solution to the device 10, the molecules 24 of the dye are in a relatively inactive or partially active fluorescent state. An electrical bias is now applied across the surface 26 of the conductor 16, causing the electrolysis reaction to occur at cathodic corrosion sites 22. The bias may be applied simply by engaging two contact probes 28 across the surface of the device 10, as shown in FIG. 2. In our experiments, we applied the bias by having the probes 28 contact the exposed metal at the bonding pads of two adjacent conductors, respectively. The bias (if <1V) may also be applied by having both probes 28 contact the same conductor 16. As shown in FIG. 2, one of the probes 28 actually contacts the conductor 16 while the other of the probes 28 may contact the passivating layer 20, if the layer 20 is relatively thin as explained further below. The probes 28 are connected to a source 30 of potential which preferably comprises a DC voltage of approximately 20 volts, although as little as 0.5 volt can be used to activate the fluorescent dye.

During the application of the bias voltage, the molecules 24 of the fluorescent dye are exposed to actinic radiation. In the present example, the IC device 10 is irradiated by a source 32 of long-wavelength ultraviolet (UV) light. Upon application of the external DC bias, fluorescence, indicated by dashed lines 34 in FIG. 2, is rapidly activated at the localized sites 22 where the electrolysis reaction is occurring. The electrolysis reaction at the sites 22 causes the release of protons by the dye molecules 24, thereby causing them to fluoresce by becoming deprotonated. Consequently, the fluorescence at such locations is greatly increased, causing the cathodic reaction sites 22 to become visibly decorated. The fluorescent intensity of the $\beta$-naphthol dye is slightly reduced from that of the $\beta$-methylumbelliferone dye, but this could be due to the fact that this molecular species fluoresces a deeper blue than the $\beta$-methylumbelliferone dye. However, identical fluorescent decoration sites are observed for the $\beta$-naphthol as for the $\beta$-methylumbelliferone dye.

The fluorescence observed was activated immediately when the bias was applied, and tended to spread out from a central point as the bias was kept on. Changes in size and shape of the sites 22 continued after initial application of the bias, with the fluorescence sites 22 spreading out more slowly after the initial activation of the fluorescent dye molecules 24. When the bias was turned off, the localized fluorescence faded much more slowly than it was activated. This technique allows one to observe how the cathodic reaction propagates after the DC bias is applied and how the perimeter of the reaction area recedes after the bias is turned off. A comparison of the fluorescence activated sites 22 of the IC device 10 with visual inspection of the device 10 revealed that localized fluorescence was present at some but not all obvious defects on the IC device 10. Also, localized fluorescence was observed at sites 22 where no visually apparent defect was present. We also observed small gas bubbles emanating from the localized sites 22 exhibiting fluorescence. This observation is evidence that the present novel decorating technique is truly detecting cathodic reaction sites, as the apparent identity of the gas bubbles is hydrogen.

The importance of the humid or moist ambient required to observe fluorescence should be emphasized for this decorating technique. Presumably, the moisture present on the surface of the device 10 is essential to produce the correct conditions to activate certain fluorescent dyes. The fluorescent dyes considered here are activated by loss of a proton from the molecule. Consequently, when the depositing step is performed by coating the surface of the passivating layer 20 with the dye molecules 24, the layer 20 should be thin enough to allow the ambient humidity to permeate the layer 20 sufficiently to give the $H^+$ ions mobility to the surface 26 of the conductor 16. This transfer mechanism may require water adsorbed on the surface of the IC device 10. Even under high humidity conditions, not all fluorescent dyes perform well. Fluorescein, although exhibiting a bright green fluorescence when applied to the device 10 (i.e., before the ethanol solvent evaporates) can not be used that effectively. Its fluorescent intensity is quite sensitive to the amount of solvent present and diminishes drastically with solvent evaporation. However, for a short period of time, as the solvent is evaporating, localized fluorescence can be activated for the fluorescein dye by external bias. The fluorescent dyes $\beta$-methylumbelliferone and $\beta$-naphthol are preferable. They exhibit better drying properties and localized fluorescence can be observed for long periods of time after their application to the IC device 10.

The application solvent for decorating the IC device 10 with the dye molecules 24 is important. Although we have been able to observe fluorescence using $\beta$-methylumbelliferone and $\beta$-naphthol dyes with an application solution employing pure ethanol, the performance of the solvent dye can be improved with the use of wetting agents. An effective dye solution is one which contains a small amount of a non-volatile solvent such as glycerol in an excess of ethanol. The concentration of glycerol in the solution must be kept relatively low. A solution having a concentration greater than about 1 percent glycerol, by volume, in ethanol will not dry sufficiently after its application. Glycerol concentrations less than 1 volume percent are satisfactory, and we prefer to use a concentration between about 0.2 volume percent and about 1 volume percent glycerol. The concentration of fluorescent dye in this solution may be between about 0.3 and about 0.6 grams/liter.

When glycerol is chosen as the non-volatile solvent, a surfactant should be added to the solution. Glycerol has a very high surface tension and does not flow well over the surface of the device 10 to form a uniform film. Adding a surfactant to the dye solution eliminates this problem. Any compatible surfactant may be used except that the effective concentration of the surfactant may be different for different materials. In the present example, we used a surfactant in the solution identified by the trade designation FC-93 which is available from the 3M Company, Minneapolis, Minn. The concentration of the surfactant in the solution was about 0.1 percent by volume. A stronger fluorescent intensity was observed with the use of this application solution. Because of the increased fluorescent intensity, the smaller localized corrosion sites could be detected with less difficulty.

The fluorescent dye molecules 24 may be subsequently removed from the IC device 10 with an acetone rinse. However, after using the acetone rinse, the device 10 should be allowed to equilibrate with the humid ambient to restore bound water to the surface before retesting the device 10 for cathodic corrosion.

The essence of the present novel method resides in the discovery that the cathodic electrolysis reaction caused by the applied electrical bias, consumes sufficient $H^+$ ions to change the ambient pH significantly enough to cause fluorescence in certain dyes. Upon application of the electrical bias, the fluorescent dye molecules 24 decorate the corrosion sites 22. More specifically, they decorate the sites 22 of the cathodic reactions. Hydrogen production at the sites 22 ($2H^+ + 2e^- \rightarrow H_2$) reduces the $H^+$ concentration at the sites, thus activating the fluorescent dye. β-naphthol is activated in aqueous solution at pH above 8.6 and β-methylumbelliferone at pH above 7.5. In similar experiments with fluorescein dye and gold metal, the fluorescence was quenched at the anode, indicating that the pH at the anode was less than 4.0. The change in pH at the cathodic reaction sites spreads out rapidly from the central defect, producing the initial visible reaction site. The slow deactivation of the fluorescent dye after the bias is turned off indicates that the pH at the cathodic reaction site reverts to its original state slowly. Either the corrosion reaction has some inertia after the applied bias is turned off and slows down gradually, and/or the diffusion of $H^+$ ions into the reaction region or $OH^-$ ions out of the region is slow.

We have discovered an effective decoration technique utilizing fluorescent dyes that can identify cathodic corrosion sites on metallized substrates. The loss of a proton from the fluorescent dye is required to produce fluorescence. Fluorescence can be activated at relatively low external bias voltages of the order of 0.5 volt. This loss of a proton and the dye molecule's subsequent fluorescent behavior appears to be an effective way to detect a cathodic corrosion site on an IC device. From our observations it appears that the fluorescent dye can detect corrosion sites not apparent upon normal visual observation. The specific defects that produce corrosion sites can then be identified. The course of the cathodic reaction in relation to the application of the external bias can also be followed. This technique can be used to provide valuable information about IC device reliability as well as for corrosion processes in general.

What is claimed is:

1. A method of detecting a cathodic corrosion site on a metallized substrate comprising the steps of:

depositing a relatively thin film of molecules of a pH sensitive fluorescent dye adjacent a metallic surface of said substrate, said metallic surface having a corrosion site thereon characterized by a reduction of the hydronium ion to hydrogen ($2H^+ + 2e^- \rightarrow H_2$) in a moist ambient capable of supplying $H^+$ ions, applying an electrical bias across said surface by engaging two contact probes across the surface of said substrate, said electrical bias being sufficient to cause an electrolysis reaction to occur at said corrosion site, and exposing said fluorescent dye to actinic radiation, whereby fluorescence is activated at the cathodic corrosion site.

2. A method as recited in claim 1 wherein said fluorescent dye is selected from the group consisting of β-methylumbelliferone and β-naphthol.

3. A method as recited in claim 2 wherein said depositing step is performed by coating said metallic surface with about $2 \times 10^{-4}$ moles of said dye dissolved in a solvent.

4. A method as recited in claim 3 wherein said solvent comprises an excess of ethanol.

5. A method as recited in claim 4 wherein said solvent further includes a non-volatile solvent and a surfactant.

6. A method as recited in claim 5 wherein said non-volatile solvent comprises glycerol having a concentration in the ethanol of between about 0.2 volume percent and about 1.0 volume percent.

7. A method as recited in claim 1 wherein a relatively thin layer of insulating material is disposed on said metallic surface and wherein said depositing step is performed by coating the surface of said insulating layer with said dye.

8. A method as recited in claim 1 wherein said electrical bias comprises a DC voltage greater than about 0.5 volt.

9. A method as recited in claim 1 wherein said actinic radiation comprises ultraviolet (UV) light, and wherein said metallic surface comprises aluminum.

10. A method as recited in claim 1 further comprising carrying out said applying and exposing steps in an atmosphere of controlled relative humidity greater than about 30 percent.

11. A method as recited in claim 1 wherein said metallized substrate comprises an integrated circuit (IC) device having metallic conductors disposed over an insulating layer, and wherein said applying step is performed by having two biasing probes contact two adjacent conductors of said device, respectively.

* * * * *